United States Patent
Feinbloom et al.

(10) Patent No.: US 12,038,630 B1
(45) Date of Patent: Jul. 16, 2024

(54) TELESCOPIC IMAGE CAPTURE/RECORDING DEVICE

(71) Applicant: Designs for Vision, Inc., Bohemia, NY (US)

(72) Inventors: Richard E. Feinbloom, New York, NY (US); Moty Solomon, Beit uziel (IL)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 18/102,747

(22) Filed: Jan. 29, 2023

(51) Int. Cl.
| | |
|---|---|
| *G02C 9/04* | (2006.01) |
| *G02B 21/18* | (2006.01) |
| *G02B 21/36* | (2006.01) |
| *G02B 23/08* | (2006.01) |
| *G02B 23/14* | (2006.01) |
| *G02B 23/16* | (2006.01) |
| *G02B 25/00* | (2006.01) |
| *G02B 27/14* | (2006.01) |
| *A61B 90/00* | (2016.01) |

(Continued)

(52) U.S. Cl.
CPC .............. *G02C 9/04* (2013.01); *G02B 21/18* (2013.01); *G02B 21/361* (2013.01); *G02B 21/362* (2013.01); *G02B 23/08* (2013.01); *G02B 23/14* (2013.01); *G02B 23/16* (2013.01); *G02B 25/004* (2013.01); *G02B 25/007* (2013.01); *G02B 25/008* (2013.01); *G02B 27/144* (2013.01); *A61B 90/361* (2016.02); *G02B 5/20* (2013.01); *G02B 25/001* (2013.01); *H04N 7/183* (2013.01)

(58) Field of Classification Search
CPC .. G02B 21/18–22; G02B 23/04; G02B 23/08; G02B 23/10; G02B 23/105; G02B 23/12; G02B 23/125; G02B 23/14; G02B 25/001; G02B 25/004; G02B 25/007; G02B 25/008; G02B 25/02; G02B 27/106; G02B 27/108; G02B 27/14; G02B 27/141; G02B 27/142; G02B 27/143; G02B 27/144; G02B 27/149; G02B 27/126; G02B 27/16; G02B 27/283; G02B 13/16
See application file for complete search history.

(56) References Cited

U.S. PATENT DOCUMENTS

| | | | |
|---|---|---|---|
| 2,246,817 A | * | 6/1941 | Sauer ...................... G01J 1/12 359/489.09 |
| 2,986,969 A | | 6/1961 | Muncheryan |
| 3,273,456 A | | 9/1966 | Feinbloom |

(Continued)

FOREIGN PATENT DOCUMENTS

| | | | |
|---|---|---|---|
| WO | WO 9215039 | 9/1992 | |
| WO | WO-2022005404 A1 * | 1/2022 | ............. G02B 23/04 |

*Primary Examiner* — Nicholas R. Pasko
(74) *Attorney, Agent, or Firm* — Law Office of Carl Giordano, PC

(57) ABSTRACT

A telescopic/image capture device that allows for the concurrent viewing and capturing an image of an object, wherein the captured image is magnified to the same level than that of the viewed image. Further included are filters incorporated into the device to allow for the attenuation of light in undesired wavelengths while allowing light in desired wavelengths to pass unattenuated. In still a further aspect of the invention, a second telescopic lens is incorporated into the path of light to be captured by the image capture device, wherein the image captured and recorded is of a greater magnification than that of the user viewable image.

20 Claims, 9 Drawing Sheets

(51) Int. Cl.
*G02B 5/20* (2006.01)
*H04N 7/18* (2006.01)

(56) References Cited

U.S. PATENT DOCUMENTS

| | | | |
|---|---|---|---|
| 3,519,339 A | 7/1970 | Hutchinson | |
| 4,511,225 A | 4/1985 | Lipson | |
| 4,544,250 A * | 10/1985 | Tanaka | G02B 13/00 396/73 |
| 5,018,846 A * | 5/1991 | Gutridge | G02B 21/18 359/372 |
| 5,042,930 A * | 8/1991 | Hutt | G02B 7/002 348/E5.029 |
| 5,078,469 A * | 1/1992 | Clark | A61B 90/361 351/158 |
| 5,162,647 A | 11/1992 | Field, Jr. | |
| 5,331,357 A | 7/1994 | Cooley | |
| 5,668,661 A * | 9/1997 | Tomioka | G02B 21/22 359/368 |
| 5,742,434 A * | 4/1998 | Carmeli | G02B 23/125 359/640 |
| 6,546,208 B1 * | 4/2003 | Costales | G02B 23/04 359/464 |
| 6,697,195 B2 | 2/2004 | Weber | |
| 7,409,792 B2 * | 8/2008 | Narcy | F41G 1/32 42/120 |
| 7,690,806 B2 | 4/2010 | Feinbloom | |
| 8,120,847 B2 | 2/2012 | Chang | |
| 8,215,791 B2 | 7/2012 | Feinbloom | |
| 8,922,624 B2 * | 12/2014 | Pretorius | G02B 21/22 348/46 |
| RE46,463 E | 7/2017 | Feinbloom | |
| 9,791,138 B1 | 10/2017 | Feinbloom | |
| 10,061,115 B2 | 8/2018 | Feinbloom | |
| 10,132,483 B1 | 11/2018 | Feinbloom | |
| 10,146,039 B2 * | 12/2018 | Schnitzler | G02B 21/006 |
| 10,146,063 B2 * | 12/2018 | Kammans | G02B 17/008 |
| 10,215,977 B1 | 2/2019 | Feinbloom | |
| 10,240,769 B1 | 3/2019 | Braganca | |
| 10,247,384 B1 | 4/2019 | Feinbloom | |
| 10,437,041 B1 | 10/2019 | Feinbloom | |
| 10,698,196 B2 * | 6/2020 | Davidi | G02B 25/008 |
| 10,895,735 B1 | 1/2021 | Feinbloom | |
| 2001/0005281 A1 | 6/2001 | Yu | |
| 2005/0078364 A1 * | 4/2005 | Tseng | G02B 23/18 359/410 |
| 2008/0219654 A1 | 9/2008 | Border | |
| 2009/0040600 A1 * | 2/2009 | Vojtech | G02B 23/04 359/399 |
| 2009/0073558 A1 | 3/2009 | Jacobs | |
| 2010/0053540 A1 | 3/2010 | Blayden | |
| 2010/0210951 A1 | 8/2010 | Rahman | |
| 2010/0305436 A1 | 12/2010 | Chen | |
| 2011/0270035 A1 | 11/2011 | Gono | |
| 2012/0120636 A1 | 5/2012 | Wilt | |
| 2014/0036356 A1 | 2/2014 | Feinbloom | |
| 2014/0210972 A1 | 7/2014 | On | |
| 2015/0253589 A1 | 9/2015 | Finkman | |

* cited by examiner

TELESCOPIC IMAGE CAPTURE/RECORDING DEVICE

BACKGROUND OF THE INVENTION

Field of the Invention

This invention relates to the field of optical devices and, in particular, to an optical magnification device incorporating image capturing therein.

Background Information

Head-borne or wearable eyewear utilizing telescopic lens provide a practitioner with a magnified view of an area that the practitioner is viewing. Whether this is a patient's mouth, as in the case of a dentist, or in a body cavity, as in the case of a surgeon, the magnified view enables the practitioner to both see details that may not be viewable without the telescopic lens and provide more precise location of their instruments.

In addition, image capturing device (i.e., cameras) have allowed for the capturing and memorializing the images (photographic and/or video) viewed by a practitioner.

Smart microscopes, such as the Axiolab 5, by Carl Ziess, uses microscope cameras to capture magnified images of an area being viewed through the microscope.

However, such devices are large, stationary and expensive and, generally used by pathologists to analyze segments that may be taken outside of the arena the procedure is occurring. The smart microscope fails to provide for the real-time capturing of a magnified image during a procedure (e. g., open-heart surgery) that assists the practitioner in performing the procedure.

Hence, there is a need in the industry for the capturing of photographic and/or video images, in real-time, during dental or medical procedures that may be used to assist and memorialize the procedure being performed.

SUMMARY OF THE INVENTION

Disclosed is a user-wearable device comprising telescopic lens and image capturing devices that allows for the capturing of images with the same magnification level as that of the telescopic lens.

Disclosed is a magnification device comprising a magnification and filtering system that allows for the viewing and capturing of a same image within selected light wavelength ranges.

Disclosed is a magnification device incorporating an image capture device to allow the magnified viewing of an object and the concurrent capturing of a photo or video of the magnified object that is the same as that being viewed.

Disclosed is a magnification device for viewing a magnified image of an object and an image capture device for the concurrent capturing of a further magnified photo or video of the object.

Disclosed is an exemplary embodiment of user-wearable device comprising a magnification lens including a filtering system that allows for the viewing and capturing of images within a desired wavelength range.

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented to clarify the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

The advantages, nature, and various additional features of the invention will appear more fully upon consideration of the illustrative embodiments described in detail in connection with the accompanying drawings, where like or similar reference numerals are used to identify like or similar elements throughout the drawings.

It is to be understood that the figures, which are not drawn to scale, and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements are not provided herein. The disclosure, herein, is directed also to variations and modifications known to those skilled in the art.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description, herein, should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instance, the terms "about" may include numbers that are rounded (or lowered) to the nearest significant figure.

Figure 1:
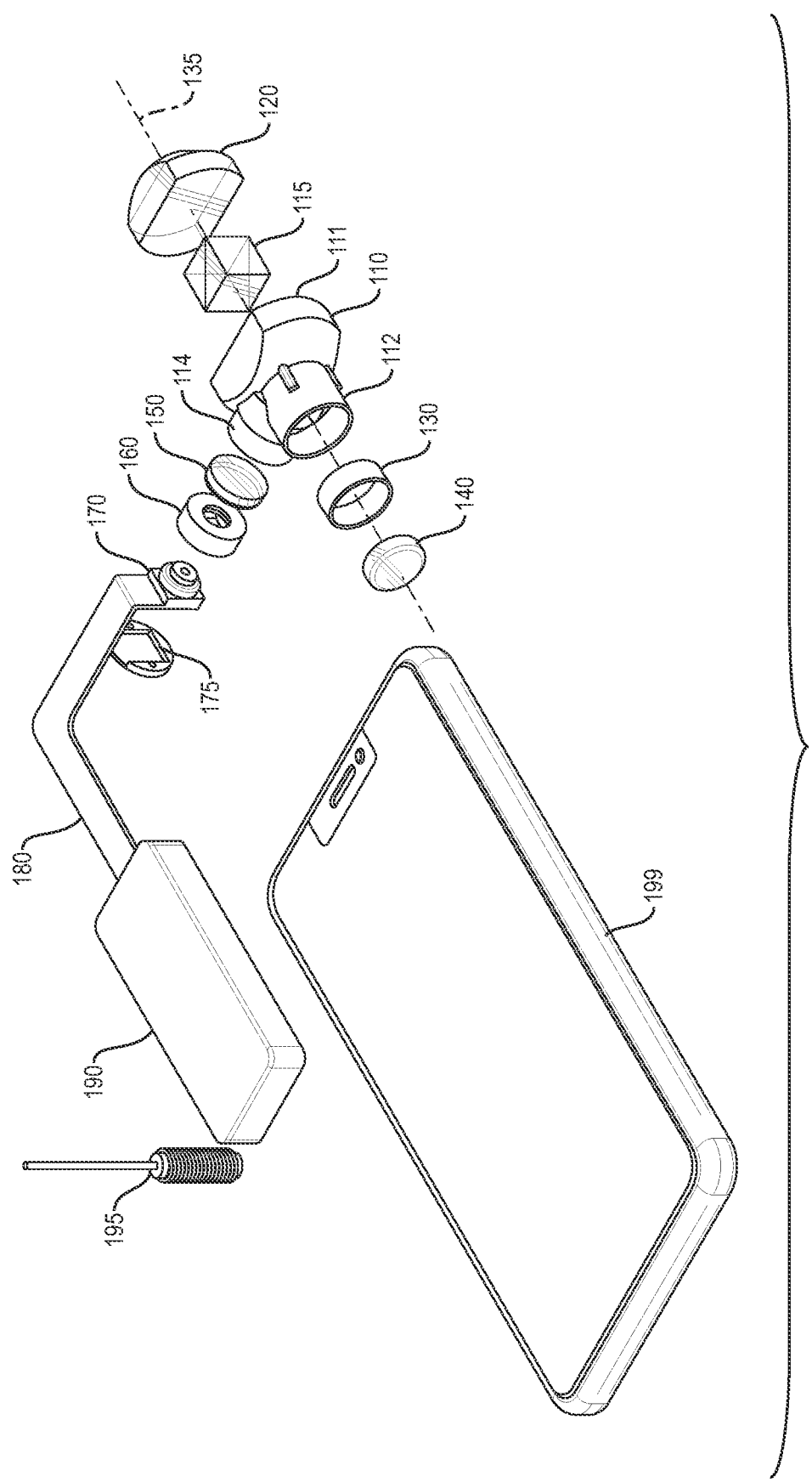
FIG. 1 illustrates an exploded perspective view of a first aspect of a first exemplary embodiment of a telescopic/image capturing device in accordance with the principles of the invention.

FIG. 1 illustrates an exploded perspective view of a first aspect of a first exemplary embodiment of telescopic/image capture device 100 in accordance with the principles of the invention.

Telescopic/image capture device 100 comprises housing 110 including a distal anterior end 111 into which may be place objective lens 120 and proximal posterior end 112 into which may be place eye-lens housing 130. Objective lens 120 and eye-lens 140 form a first magnification (or telescopic) system that allows for the enlarged viewing of an object (not shown) when the object is placed along the optical axis 135 formed by objective lens 120 and eye-lens 140 at a known distance (e.g., 12-20 inches) from the objective lens 120.

Further illustrated is second end 114, positioned substantially perpendicular to an optical axis 135 positioned between anterior end 111 and posterior end 112 of housing 110. Within second end 114 is positioned second eye-lens 150 and camera housing 160. Within camera housing 160 is further positioned an image capture module (e. g., camera, charged coupled device (CCD) and a complementary metal-oxide semiconductor sensor (CMOS), etc.) 170. Eye-lens 140 and second eye-lens 150 have substantially same optical properties (e.g., focal lens, curvature, etc.) such that the first magnification device formed by the combination of objective lens 120 and eye-lens 140 is the same as a second magnification device formed by the combination of objective lens 120 and eye-lens 150.

Camera opening 114 is closed by camera cap 175 such that objective lens 120, eye-lens 140 and camera cap 175 seal telescopic/image capture device 100 to prevent dust or damage to the elements of device 100.

Further positioned within housing 110 is beam splitter or light director 115. Beam splitter or light director 115 is positioned within housing 110 to direct light (i.e., the image being viewed) entering objective lens 120 to both eye-lens 140 and second eye-lens 150. Accordingly, splitter 115 is arranged within housing 110 at a point to direct light toward second eye-lens 150. In one aspect of the invention, beam splitter 115 may split the incoming light (for example, evenly, i.e., 50/50 split) between eye-lens 140 and second eye-lens 150 such that the light intensity viewed through eye-lens 140 is substantially the same as the light intensity viewed through second eye-lens 150. Alternatively, beam splitter 115 may split the incoming light in other ratios. For example, 60/40, 70/30, 80/20, 90/10, wherein the greater or larger amount of light is passed through beam splitter 115 toward eye-lens 140 and the remaining (lesser) amount being directed by beam splitter 115 toward second eye-lens 150. In one aspect of the invention, the greater sensitivity of the image capturing capability of camera module 170 allows for an unequal split of the light entering objective lens 120.

Although FIG. 1 illustrates splitter 115 as being a block-shaped element (i.e., block beam splitter) it would be recognized that splitter 115 may comprise a plate beam splitter or mirror assembly where the mirror is partially transmissive and partially reflective and oriented at a forty-five (45) degree angle. In one aspect of the invention, housing extension 114 is positioned, and sized, with respect to housing 110 to enable the distance between second eye-lens 150 and objective lens 120 to be substantially the same as the distance between objective lens 120 and eye-lens 140. Hence, the magnification of the image of the object being viewed through second eye-lens 150 is substantially the same as the magnification of the image of the object being viewed through eye-lens 140.

In accordance with the principles of the invention, the images captured by image capture device 170 are, thus, the same as those viewed by a user (not shown) through eye-lens 140.

Further illustrated is transmitter 190 in communication with image capture device 170, through a wire-ed connection 180. Transmitter 190, including antenna 195. is configured to transmit the captured images through second magnification device (i.e., objective lens 120 and second eye-lens 150) to a receiving/storage/display system 199; in this illustrated example, a cellular phone, however it would be understood that system 199 may be one of: a laptop computer, a stand-alone server system, a cloud-based server system, a display, a storage device and other similar systems used for storing and/or displaying images. The captured images/video may then be displayed, stored the captured image and/or be further processed to improve color, magnification, etc.

In addition, receiver 199 may further transmit the captured images to one or more devices using conventional cellular and/or local area network protocols (i.e., Wi-Fi, which utilizes one or more of the IEEE 802.11 family standard protocols).

Alternatively, transmitter 190 may transmit the captured images directly to other types of receiving systems such as a computing system, a network server, a cloud-based server, etc. that may display the captured images on a computer monitor or on a television screen. In one aspect of the invention, the transmission of the captured image, through transmitter 190, may be accomplished using one or more known wireless communication protocols. For example, near-field communication protocol (e. g., Zigbee), or BLUETOOTH, which allows a known separation between transmitter 190 and the intended receiver 199. Alternatively, transmitter 190 may transmit the captured images using Wi-Fi protocol that allows for a greater separation between transmitter 190 and the intended receiver 199. In still another embodiment, transmitter 190 may include a connector (e.g., HDMI, USB-c, etc.) that may attach to a wire-ed connector (not shown) that may transmit captured images/video to a receiving system (e.g., illustrated cellular phone 199, a computing system, etc.) through a wire-ed connection.

Although a wired connection 180 is shown as separating camera module 170 and transmitter 190, it would be recognized that transmitter 190 may be incorporated onto camera module 170 to transmit captured images to, for example, the illustrated receiving system 199.

Similarly, module 170 may be directly wired to one or more receiving devices that receive the captured images.

Figure 2:
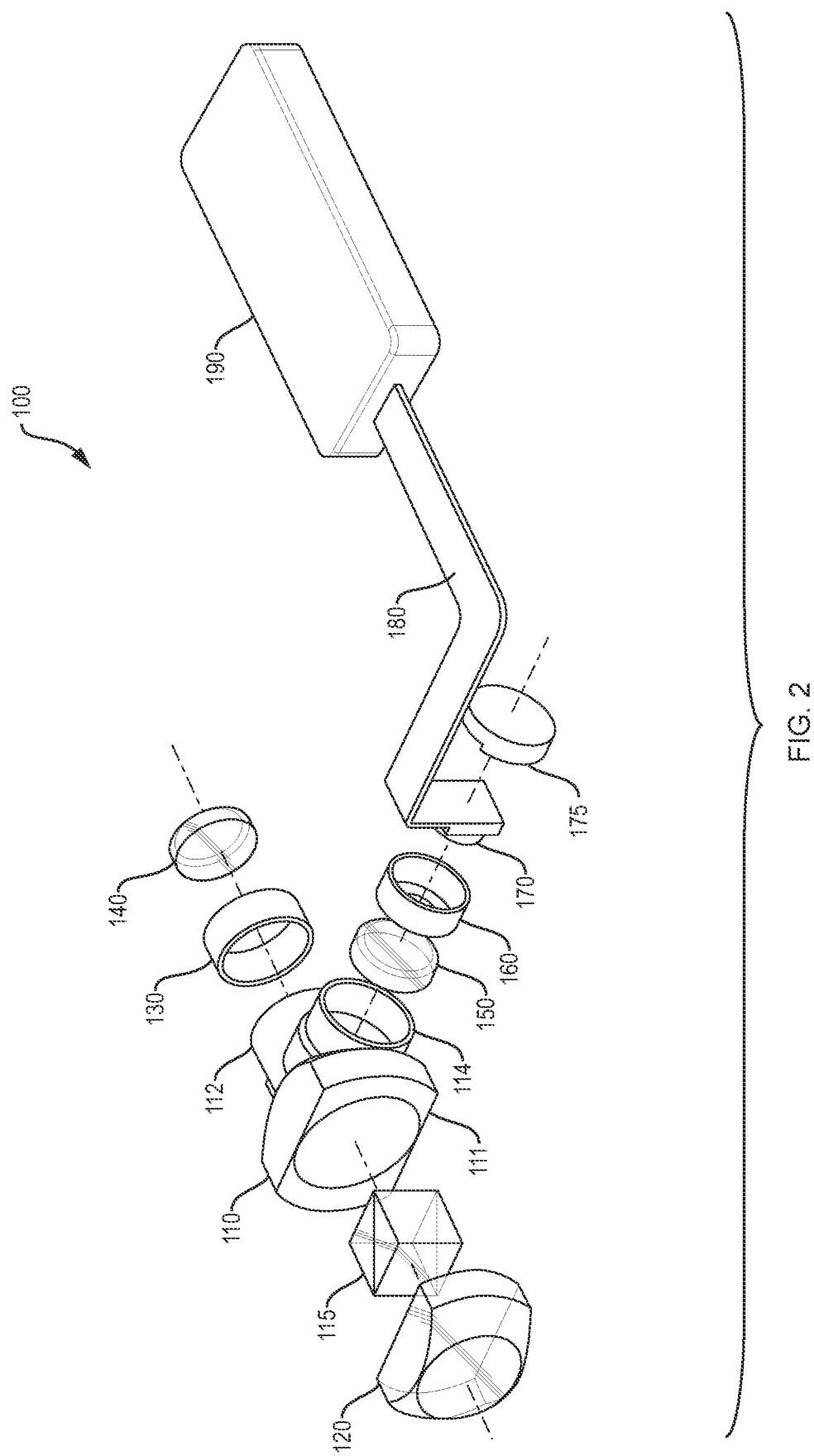
FIG. 2 illustrates a second exploded perspective view of the first exemplary embodiment shown in FIG. 1

FIG. 2 illustrates a second exploded perspective view of the first exemplary embodiment shown in FIG. 1. In second perspective view of magnification/image capture device 100 is shown, beam splitter 115 within housing 110 and objective lens 120 positioned at a distal end 111 of housing 110. Further illustrated is eye-lens 140 positioned within a proximal end 112 of housing 110 and extension 114 positioned between proximal end 111 and distal end 112 into which is inserted second eye-lens 150 and image capture device 170.

In accordance with the principles of the invention, the positioning of housing extension 114 with respect to housing 110 would be understood by those skilled in the art to be based on maintaining a substantially equal distance between objective lens 120 and eye-lens 140 and objective lens 120 and second eye-lens 150 to allow for a substantially same level of magnification.

Further illustrated are eye-lens housing 130 and second eye-lens housing 160 into which eye-lens 140 and second eye-lens 150, respectively, may be incorporated. Eye-lens housing 130 and camera housing 160 may be slidable within corresponding ones of proximal end 112 and housing extension 114 to render the distance between objective lens 120 and eye-lens 140 substantially the same as the distance between objective lens 120 and second eye-lens 150. Eye-lens housing 130 and camera eye-lens housing 160 may be collimated and glued in place once the appropriate distances are established. In another aspect of the invention, proximal end 112 and housing extension 114 may include a screw thread into which corresponding eye-lens housing 130 and camera housing 160, each with a corresponding screw thread, may be positioned within housing 110. Although a slidably arrangement or a screw thread configuration is discussed, it would be recognized that other types of connections (e. g., a bayonet connection) may be incorporated into housing 110 without altering the scope of the invention.

Figure 3:
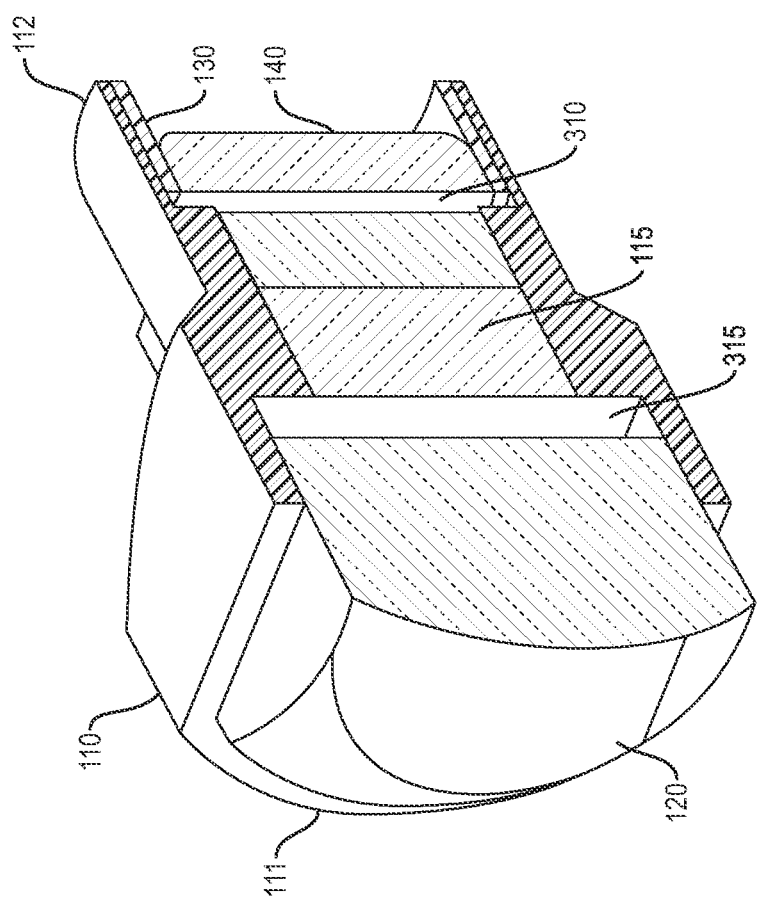
FIG. 3 illustrates a perspective cut-away side view of the telescopic/image capture device shown in FIG. 1.

FIG. 3 illustrates a perspective cutaway view of an assembled telescope/image capture device 100 shown in FIG. 1.

In this illustrated view, objective lens 120 is positioned within housing 110 and spaced apart from beam splitter 115 by spacer 315. Spacer 315 may comprise an optically clear material of a desired thickness that allows beam splitter 115 to be appropriately positioned within housing 110. Further illustrated is spacer 310, which similar to spacer 315 is of an optically clear material of a desired thickness to separate eye-lens 140 an appropriate distance from beam splitter 115. Spaces 310 and 315 and light director 115 create a distance between objective lens 120 and eye-lens 140 that determine the magnification level of device 100.

Although spacers 310 and 315 are discussed with regard to optically clear material, it would be recognized that spacers 310 and 315 may also be air gaps between the elements. In one aspect of the invention, the positioning of objective lens 130, beam splitter 115 and eye-lens 140 may be achieved by ridges along an inner surface within housing 110 that limits the movement of the contained elements therein. Thus, spacers 310 and 315 are created by the fixed placement of the referred to elements.

Further illustrated, in further detail, eye-lens housing 130, including eye-lens 140, positioned within distal end of housing 110. In this illustrated example, eye-lens housing 130 comprises a slidable engagement with respect to housing 110 and may be held in place with an adhesive material.

Figure 4:
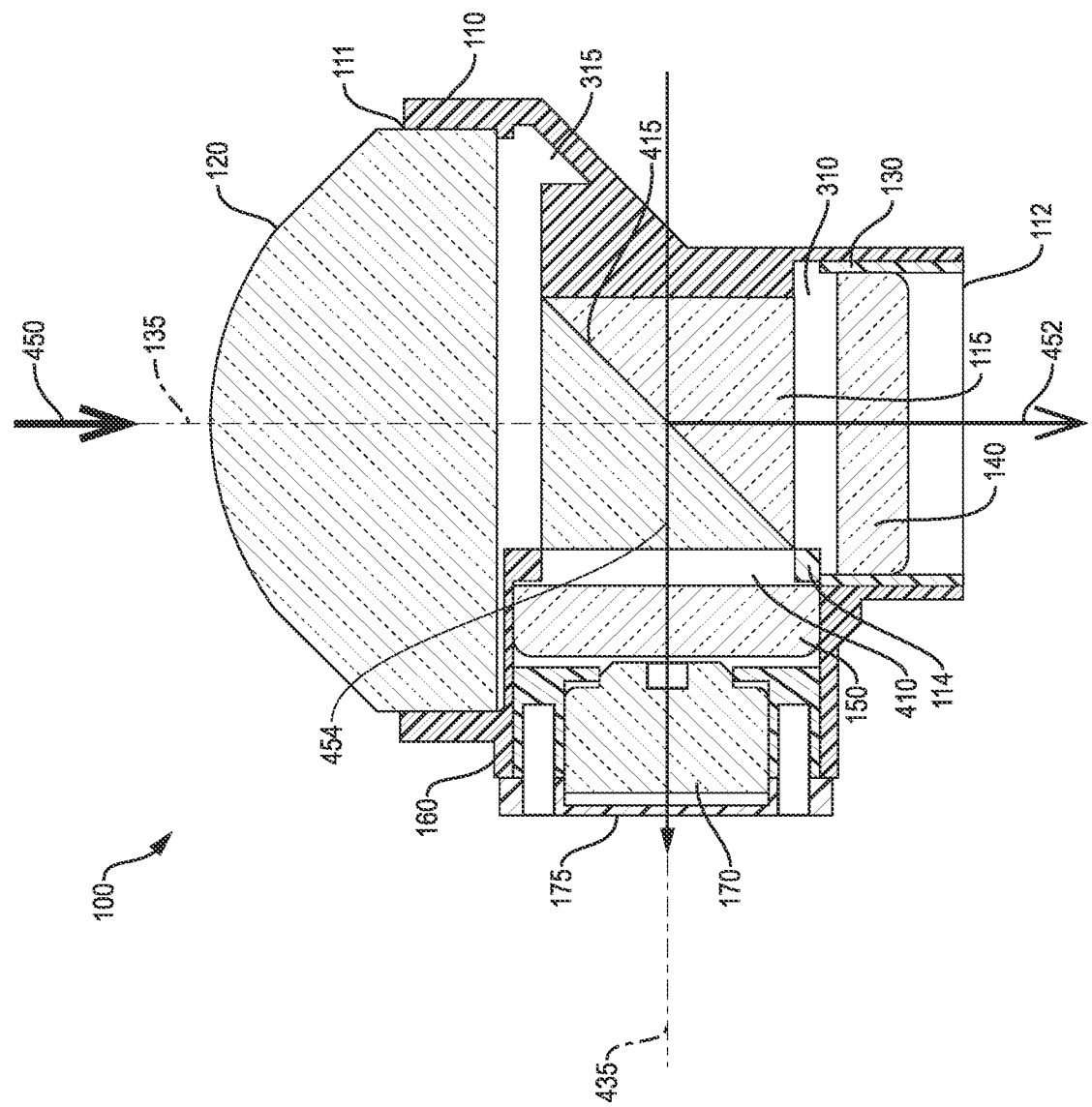
FIG. 4 illustrates a cut-away top view of the telescopic/image capture device shown in FIG. 1.

FIG. 4 illustrates a cutaway top view of an assembled telescope/image capture device 100 shown in FIG. 1.

In this illustrated view first optical axis 135 is shown extending along a longitudinal axis of telescope/image capture device 100 through objective lens 120 and eye lens 140. The separation between objective lens 120 and eye lens 140, in part, defining the magnification level of telescope/image capture device 100. Further illustrated, is second optical axis 435 extending through image capture device 170 substantially perpendicular to first optical axis 135, wherein spacer 410 positions second eye-lens 150 a known distance from beam splitter 115 so as to provide appropriate separation to enable the distance between objective lens 120 and second eye-lens 150 to be substantially the same as the distance between objective lens 120 and eye-lens 140. First optical axis 135 and second optical axis 435 intersect along (partially) reflective surface 415 associated with beam splitter 115. In accordance with the principles of the invention, light 450 associated with an image entering objective lens 120 impinges upon partially reflective surface 415 of beam splitter 115, wherein a known portion of light 452 of the input light 450 continues through reflective surface 415 toward eye-lens 140 where the image, which has been enlarged by the positioning of objective lens 120 and eye lens 140, may be viewed by a user (not shown). The remining portion of light 454 of the input light 450, which is reflected by reflective surface 415, is directed toward second eye-lens 150, where an image (or a video), which has been magnified by the positioning of objective lens 120 and second eye-lens 150, is captured by image capture device 170. In one aspect of the invention, the partially reflective surface 415 may allow for an equal distribution (50-50) of light impinging upon its surface. In another aspect of the invention, the distribution of light may allow for more light to pass through to be viewed and less light to be captured by image capture device 170. For example, reflective surface 415 may possess a transmission/reflective property of a 70/30 light distribution wherein seventy (70%) percent of the light associated with a viewed image impinging upon reflective surface 415 is passed through reflective surface 415 to be viewed by a user, while thirty (30%) percent of the light is reflected by reflective surface 415 toward image capture device 170. Other combinations of light distribution (80/20, 60/40, etc.) may similarly be incorporated into the transmission/reflective properties without altering the scope of the invention. In still a further aspect of the invention, 90 percent of the light entering objective lens 120 may pass through to eye-lens 140 while the remaining 10 percent of the light is directed by surface 415 toward second eye-lens 150. In this illustrated example, a 75/25 split is shown by the dimensions of the light rays 450, 452 and 454

Figure 5:
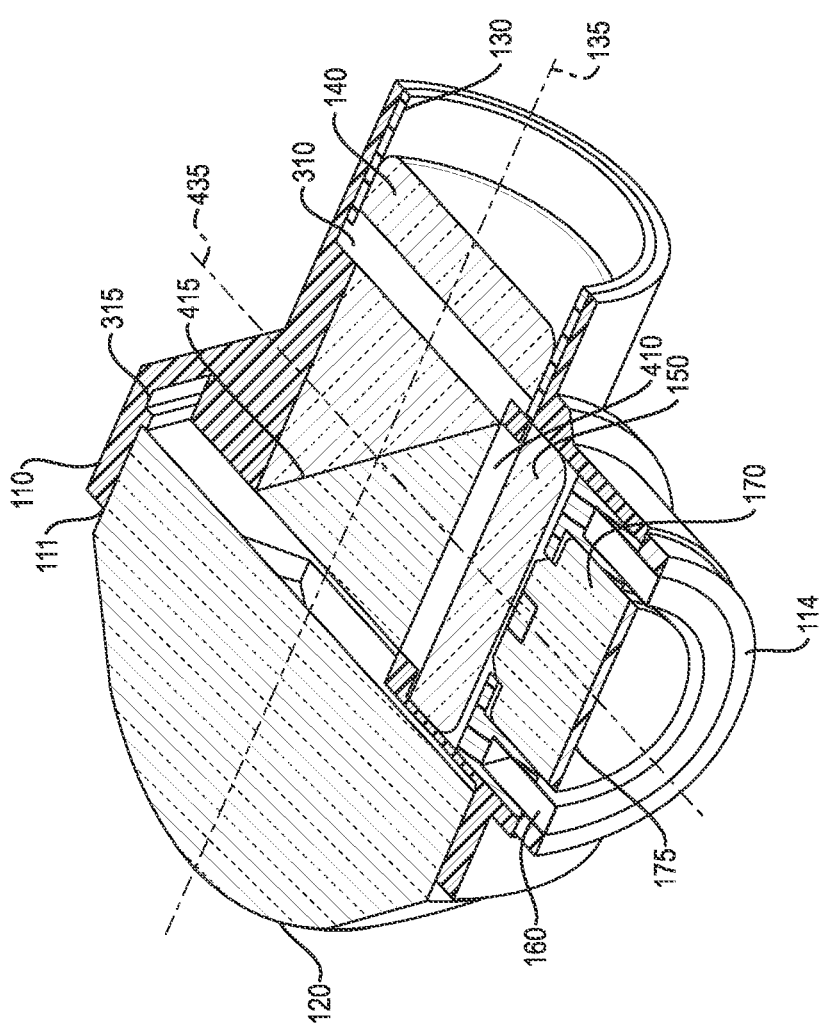
FIG. 5 illustrates a perspective view of the cut-away to view shown herein.

FIG. 5 illustrates a prospective cut-away top view of the telescopic/image capture device 100 disclosed, herein.

In this exemplary prospective top view of device 100, it is more clearly shown eye-lens 140 and lens housing 130 positioned within a distal end 112 of housing 110. Further illustrated is camera housing 160 and second eye-lens 150 and image capture device 170 positioned within housing extension 114, wherein a straight-line distance along axis 135 between objective lens 120 and eye-lens 140 is substantially the same as the distance between objective lens 120 and second eye-lens 150, when the distance the light reflected off of reflective surface 415 and along axis 435 is considered.

Figure 6:
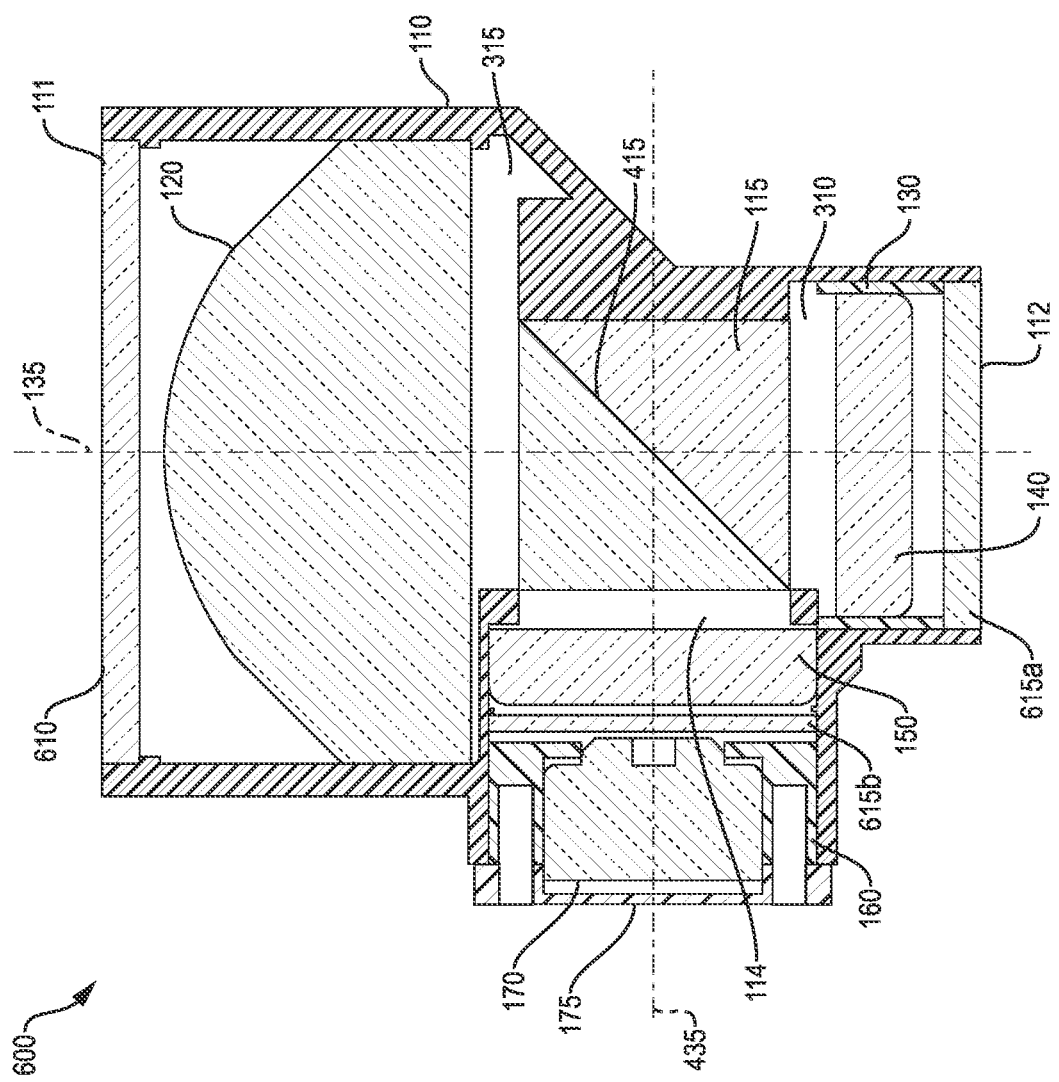
FIG. 6 illustrates a cut-away top view of a second aspect of the first exemplary embodiment a telescopic/image capture device in accordance with the principles of the invention.

FIG. 6 illustrates a cut-away top view of a second aspect of the first exemplary embodiment Shown in FIG. 1.

In this illustrated second aspect, which is similar to the configuration shown in FIG. 4, telescopic/image capture device 600 comprises objective lens 120 contained within distal end 111 of housing 110 and eye-lens 140 positioned within eye-lens housing 130 within proximal end 112. Further illustrated is second eye-lens 150 and image capture device 170 positioned within housing 160 which is positioned in housing extension 114.

In accordance with the second exemplary embodiment of a magnification device further illustrated is objective filter 610 positioned toward distal end 111 of housing 110, wherein filter 610 includes optical characteristics (e. g., optical density) to reduce or attenuate undesired light wavelengths while allowing passage of desired wavelengths. For example filter 610 may include optical characteristics that may reduce in magnitude or intensity (through absorption or reflection) light associated with a viewed image in a first wavelength range while allowing light associated with the viewed image within a second wavelength range to pass substantially unattenuated. For example, filter 610 may be configured to reduce light wavelengths associated with a viewed image or area in a first wavelength range by 80 percent and allowing 20 percent of the light within the first wavelength (i.e., residual light) and 100 percent of light within a second wavelength range to pass (i.e., unattenuated light).

Accordingly, attenuated light in the first wavelength range and the unattenuated light in the second wavelength range is then magnified based on the magnification level of combination of objective lens 120 and eye-lens 140 (or second eye-lens 150).

To reduce the residual light within the first wavelength range remaining after attenuation by filter 610, eye-lens filter 615a and second eye-lens filter 615b are introduced within the optical paths along optical axis 135 and 435, respectively. Eye-lens filter 615a and second eye-lens filter 615b each possess optical properties that reduce the intensity of the magnified residual light in the first wavelength range to a second residual magnitude while allowing light, associated with the viewed image within the second wavelength range to pass substantially unattended.

In one aspect of the invention, the optical characteristics (whether absorptive or reflective) of objective filter 610 may be determined based at least on an expected magnitude or intensity of light within a first wavelength range so as to reduce the intensity of the incoming light to a known residual magnitude and the optical characteristics (whether absorptive or reflective) of each of eye-lens filter 615a and image capture device filter 615b may be based at least on the optical characteristics of the objective filter 610, the known level of magnification of the combination of objective lens 120 and eye-lens 140, and the percent of light distribution of beam splitter 115, wherein the intensity of the magnified residual light is reduced to a second residual magnitude. In one aspect, the second residual magnitude may be selected to be below a level that may cause damage the eyes of a user viewing the image. U.S. Pat. Nos. 10,895,735 and 11,099,376, the content of both of which are incorporated by reference, herein, provides more detailed teaching regarding the selection of the optical characteristics of objective filter 610 and eye-lens filter 615a (and/or filter 615b) to reduce the intensity of an incoming light within a known wavelength band while allowing the incoming light to be substantially unattenuated in a second wavelength band. For example, U.S. Pat. No. 10,895,735 teaches the selection of optical characteristics of objective lens filters and eye-lens filters to reduce wavelength that may be harmful to a user's eyes to acceptable limits (i.e., below a known threshold) before being viewed by a human eye. U.S. Pat. No. 11,099,376 teaches the selection of optical characteristics of objective lens filters and eye-lens filters 615a, to reduce light within undesired wavelength ranges, while allowing light in desired wavelength to pass when light of multiple wavelengths bands are emitted and may impinge on objective filter 610.

In one aspect of the invention, the optical characteristics of eye-lens filter 615a and second eye-lens filter 615b may be selected to be the same or selected to be different. In one aspect of the invention, the optical characteristics of filters 615a and 615b may be different based at least in part on the characteristics of beam splitter 115, as the amount of light reaching filter 615b may be substantially less than the amount of light reaching filter 615a. Thus, while the optical characteristics of eye-lens filter 615a may be selected to reduce the magnitude of an incoming light, as reduced by the characteristics of light director 115, in a first (or undesired) wavelength range to a level that prevents the light in the wavelength range from being harmful to, or unnecessary for viewing by, a user, the optical characteristics of filter 615b may further be determined based on the sensitivity of the image capture device 170. Thus, the optical characteristics of filter 615b may be significantly different than those of filter 615a based on the reduced intensity of light entering filter 615b as a result of the beam splitting by beam splitter 115. In addition, there is a lack of need to reduce the magnitude of the light to a level that would be below a level that is harmful to a user's eye.

Figure 7:
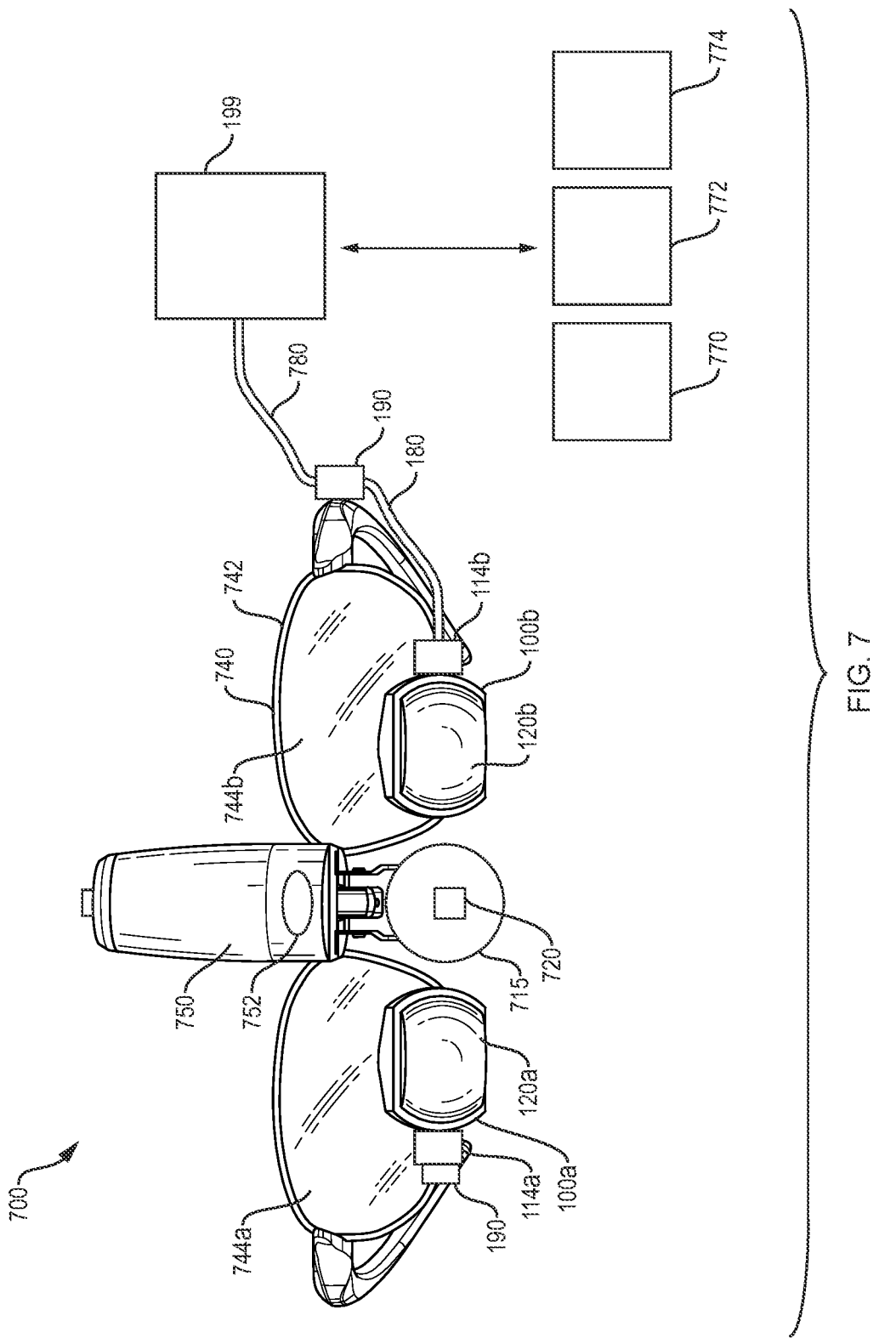
FIG. 7 illustrates an exemplary eyewear configuration incorporating the telescopic/image capture device discussed herein.

FIG. 7 illustrates an exemplary embodiment of a lighted eyewear configuration incorporating the telescopic/image capture device disclosed, herein.

Lighted eyewear configuration 700 comprises an eyewear 740 includes frame element 742, which supports first lens 744a and second lens 744b.

Further illustrated is light assembly 715 including a lighting source 720 that may be used to light an area being viewed by a user. In accordance with one aspect of the invention, lighting source 720 may comprise a lighting source emitting light in a single wavelength band (e. g., white light, blue, red, violet, green, etc.) or emitting light in multiple wavelength bands, as discussed in U.S. Pat. No. 11,099,376. In addition, the light emitted by lighting source 720 may comprise light in wavelength bands that may be harmful to the eyes of a user and, thus, must be reduced in intensity (i.e., filtered) to prevent damage to the user's eyes. Alternatively, light emitted by lighting source 720 may interfere with the light desired to be viewed.

Power may be provided to light source 720 by a constant voltage supply; in this illustrated example, a battery (not shown) contained within pod 750. Control of the voltage provided to light source 720 may be obtained through a switch 752 that may be one of a physical switch, a capacitive switch, a sensor switch or a remote switch. A physical switch may be a conventional two (2) position (on/off) switch that requires a user to physically touch the switch. A capacitive switch may comprise an electronic circuit that detects a change in capacitance when a designated region is touched or a change in an electrostatic field when an object passes nearby. A sensor switch, which may be active or passive, may, for example, detect the presence of a reflection of a transmitted signal and a remote switch may be a switch that transmits a signal to a receiver on an electric circuit that controls the application of a voltage to the lighting source.

In addition, although a battery configuration is illustrated and discussed it would be recognized that other forms of constant energy may be provided to lighting source 720. For example, a wired connection from the electronic components associated with the image capture device (not shown) within extension housing 114 within the illustrated eyewear to a remote power source (not shown), which may be one of: a battery source or an AC/DC converter may be incorporated to the eyewear 700 without undue experimentation. In one aspect of the invention, the wired connection may be removably attachable to extension housing 114. Although lighting source 720 is shown attached to eyewear 740, it would be recognized that lighting source 720 may be a separate from eyewear 740 and it would be within the knowledge of those skilled in the art of utilizing a separate lighting source.

In the exemplary configuration shown, telescope/image capture devices 100 is incorporated into lens 744a into lens 744b. Although a two telescopic/image capture devices second eye-lens 150 are shown, it would be understood that a single telescopic/image capture device 100 may be utilized in the eyewear 740, without altering the scope of the invention.

In this illustrative exemplary embodiment of the use of device 100, a first telescopic/image capture device 100, referred to as device 110a, is shown incorporated into lens 744a wherein device 110a includes transmitter 190 directly attached to extension housing 114a. Transmitter 190 transmits the collected photographic/video data from an image capture device within extension housing 114 (referred to as 114a) to receiving system 199, as discussed with regard to FIG. 1.

Receiving system 199, after receiving the photographic/video image data provides the received data to one a display system 770, a storage system 772 and a processing system 774, which may process the received data and provide a processed image to display system 770. Although receiving system 199 is shown separated from display system 770, storage system 772 and processing system 774, it would be recognized that receiving system 199 may be incorporated into display system 770, storage system 772 and processing system 774 without alternating the scope of the invention claimed.

Further illustrated is a second telescopic/image capture device 100, referred to as 100b, incorporated into lens 744b. In this exemplary configuration, image capture device (not shown) within extension housing 114 (referred to as 114b), transfers collected photographic images/video data to transmitter 190, through a wired connection 180 as is shown in FIG. 1. In this illustrated example, transmitter 190 is shown placed on frame 740. However, it would be understood that transmitter 190 may be located in any position (e.g., a belt, a shirt collar, etc.) that may be reached by a length of wired connection 180 shown. Transmitter 190, as previously discussed, transmits the received data to receiving system 199. In this illustrated example, the transmission of image date is through wire-ed connection 780 between transmitter 190 and receiving system 199.

Although a wireless and a wire-ed configuration are shown with regard to the means for transmitting collected photographic/video image data to transmitter 190 and a wireless and a wire-ed configuration to transmit photographic/video image data to receiving system 199, it would be recognized that both methods of data transfer (wired, wireless) are considered within the scope of the invention and either method may be employed without altering the scope of the invention.

Accordingly, images may be viewed and currently collected by magnification device 100a and 100b in real-time while performing a procedure (e. g., dental surgery), wherein the images are magnified by a level comparable to those that are view. The captured images are provided to transmitter 190 to be transmitted to a receiving system 199, which provides for a viewing/collection medium (e.g., a computer, a display, a cell phone, etc.). The collected images (e. g., video and photos) may then be subsequently reviewed and analyzed to insure proper treatment and/or training.

Figure 8:
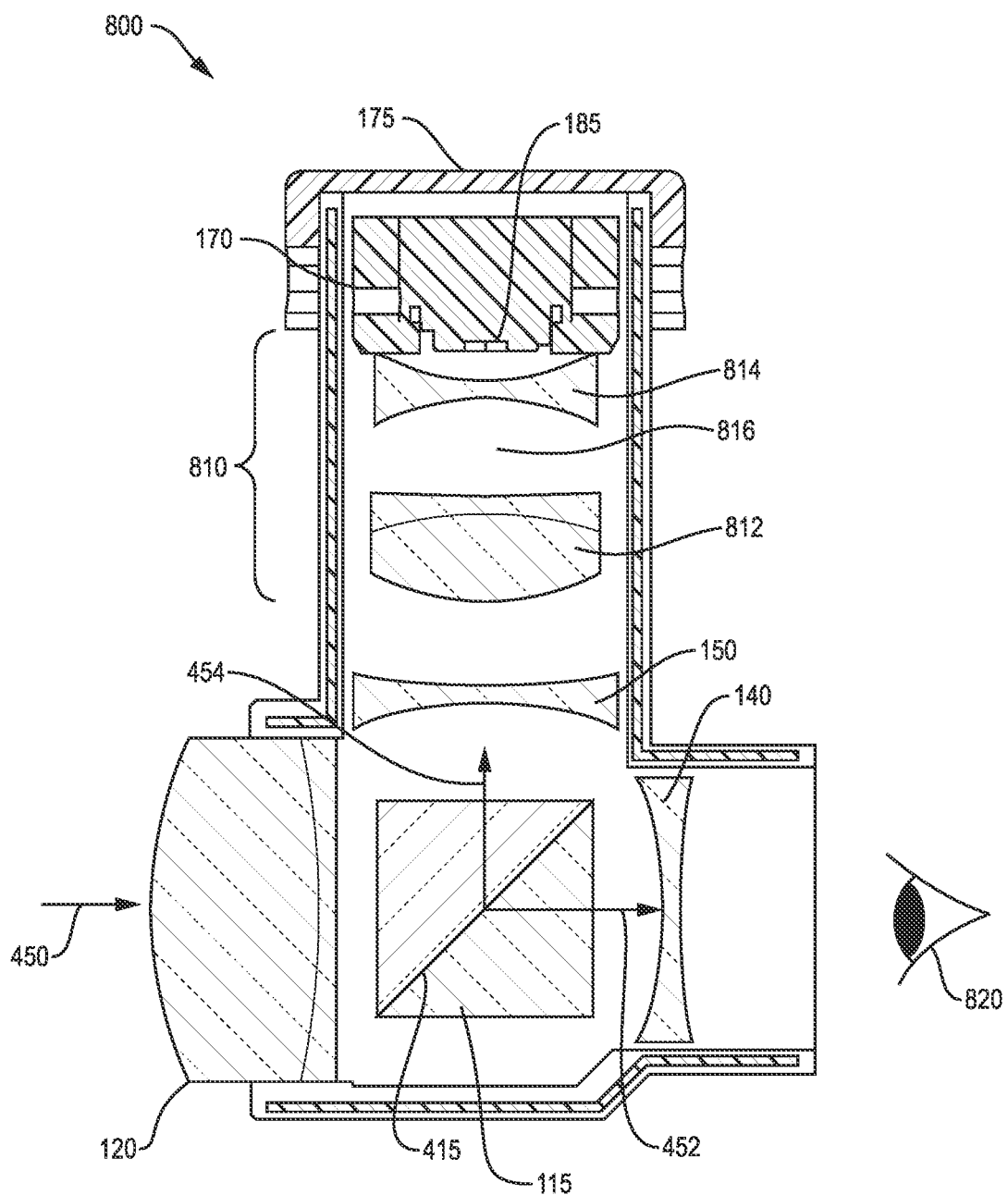
FIG. 8 illustrates a cross-sectional view of a first aspect of a second exemplary embodiment of a telescopic/image capture device in accordance with the principles of the invention.

FIG. 8 illustrates a cross-sectional view of a first aspect of a second exemplary embodiment of a telescopic/image capture device in accordance with the principles of the invention.

In this illustrated embodiment, telescopic/image capture device 800 comprises objective lens 120, splitter 115, eye lens 140 and second eye lens 150, as previously described. Further illustrated is image capture device 170 including lens 185.

In accordance with this second aspect of the invention claimed is "afocal" telescope 810 (i.e., focused at infinity) inserted between second eye lens 150 and lens 185. Afocal telescope 810 comprises a second objective lens 812 and a third eye-lens 814 separated by spacer 816. I this illustrated second embodiment, afocal telescope 810 represents a second magnification device that further magnifies the image to be captured by image capture device 170. For example, with a 2.5× (2.5 times) magnification level achieved by the optical characteristics of objective lens 120 and eye-lens 140 and the spacing therebetween, and a similar level of magnification (2.5×) between objective lens 120 and second eye-lens 150, afocal telescope 810 provides a further level of magnification of the viewed image. For example, a 2 times (2×). Accordingly, images viewed by device 170 provides for a five times (5×) magnification of the collected image.

Figure 9:
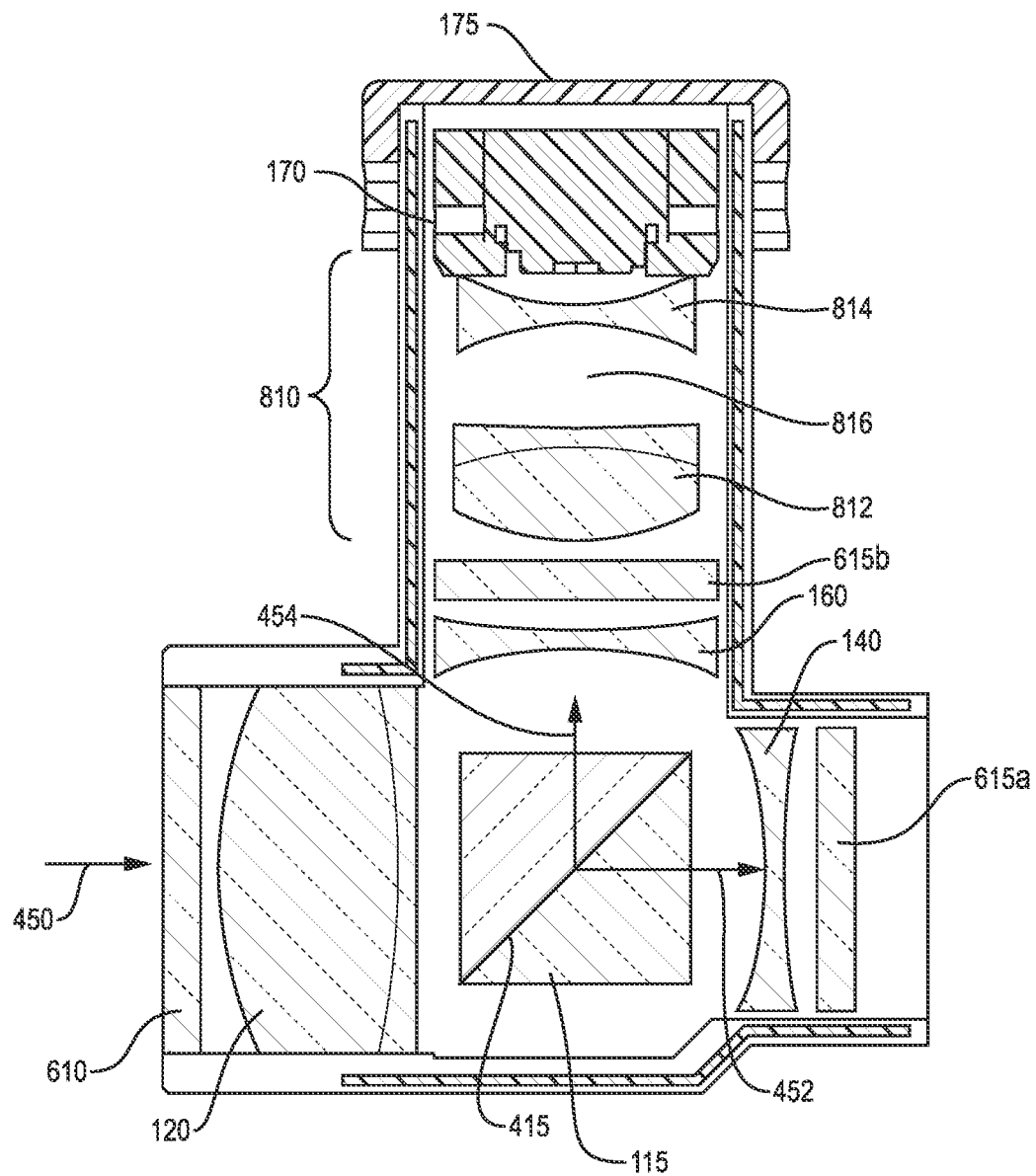
FIG. 9 illustrates a cross-sectional view of a second aspect of a second exemplary embodiment of a telescopic/image capture device in accordance with the principles of the invention.

FIG. 9 illustrates a cross-sectional view of a second aspect of the second exemplary embodiment of a telescopic/image capture shown in FIG. 8.

In this illustrated aspect of the invention 900, filters 610, 615a and 615b, which were previously discussed, are incorporated into device 800 shown in FIG. 8. Operation of the magnification device 900 is comparable to that of FIG. 8 with the additional feature of selecting filtering characteristics that limit the wavelength range viewed by user 820 and image capture device 170, as discussed with regard to FIG. 6.

In summary, a telescopic/image capture device is disclosed that allows for the concurrent viewing and image capturing of an object, wherein the captured image is magnified to same level as that of the viewed image. Furthermore, filters are incorporated into the device to allow for the attenuation of light in undesired wavelengths while allowing light in desired wavelengths to pass unattenuated. In still a further aspect of the invention, a second telescopic lens is incorporated into the path of light to be captured by the image capture device, wherein the image capture and recorded is of a greater magnification than that of the user viewable image.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above regarding specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. A magnification/recording device comprising:
a housing comprising:
a first magnification system comprising:
an objective lens positioned within a distal end of said housing; and
an eye-lens positioned within a proximal end of said housing, said objective lens and said eye-lens being separated by a known distance, wherein said separation of said objective lens and said eye-lens achieving a known level of magnification of an object being viewed by said first magnification device along a first optical axis formed by said objective lens and said eye-lens;
a housing extension, extending perpendicular to said housing, said housing extension containing therein:
a second eye-lens, said objective lens and said second eye-lens forming a second magnification device along a second optical axis, said second optical axis being perpendicular to said first optical axis, wherein an optical distance between said objective lens and said second eye-lens and an optical distance between objective lens and said eye-lens is the same such that a magnification level of said second magnification device is the same as the known level of magnification of the first magnification device; and
an image capture device configured to:
capture an image of said object; and
a light director, positioned within said housing at an intersection of said first optical axis and said second optical axis, said light director, configured to:
transmit a known amount of light entering said objective lens toward said eye-lens along said first optical axis; and
reflect a remainder of said light entering said objective lens toward said second eye-lens along said second optical axis, wherein said image of said object captured by said image capture device is comparable to an image of said object viewed through said first magnification device.

2. The magnification/recording device of claim 1 further comprising:
an afocal magnification device, said afocal magnification device configured to:
magnify said remainder of said light after passing through said second magnification device.

3. The magnification/recording device of claim 1, wherein said known amount of light is greater than or equal to fifty (50) percent of said light entering said objective lens.

4. The magnification/recording device of claim 1, wherein said known amount of light within a range of 51 and 95 percent of said light entering said objective lens.

5. The magnification/recording device of claim 1 further comprising:
a transmitter configured to:
transfer images captured by said image capture device to a receiving system, wherein said transfer is through one of: a wired connection and a wireless connection.

6. The magnification/recording device of claim 1, wherein said image capture device comprises one of: a charged coupled device (CCD) and a complementary metal-oxide semiconductor sensor (CMOS).

7. The magnification/recording device of claim 1, wherein said light director is one of: a block beam splitter, a plate beam splitter and a partially transmissive and partially reflective mirror assembly.

8. The magnification/recording device of claim 1, wherein said first magnification device is focused at a known distance from said objective lens.

9. The magnification/recording device of claim 1, comprising:
an objective filter placed before said objective lens, said objective filter configured to:
attenuate said light entering said objective lens, in a first wavelength range to a reduced amplitude, wherein said light is attenuated prior to said light entering said objective lens; and
allow passage of said light in a second wavelength range.

10. The magnification/recording device of claim 9, comprising;
an eye-lens filter placed after said eye-lens, wherein said eye-lens filter is configured to:
attenuate said reduced amplitude of light in said first wavelength range after said reduced amplitude of light in said first wavelength has been magnified by said known level of magnification, wherein an optical density of said eye-lens filter is based on an optical density of said objective filter and said known level of magnification; and
a second eye-lens filter after said second eye-lens, wherein said second eye-lens filter is configured to:
attenuate said reduced amplitude of light in said first wavelength range after said reduced amplitude of light in said first wavelength has been magnified by said known level of magnification.

11. The magnification/recording device of claim 10, wherein an optical density of said eye-lens filter is one of: a same as, and different than, an optical density of said second eye-lens filter.

12. A viewing/recording device comprising:
an eyewear comprising:
a left lens;
a right lens; and
a magnification/recording device incorporated into at least one of said left lens and said right lens, wherein said magnification/recording device comprises:
a first magnification device comprising
an objective lens positioned at a distal end of said first magnification device; and
an eye-lens positioned at a proximal end of said first magnification device, said objective lens and said eye-lens being separated by a known distance, wherein said separation of said objective lens and said eye-lens achieving a known level of magnification of an object being viewed by said first magnification device along a first optical axis formed by said objective lens and said eye-lens;
a second magnification device comprising:
a second eye-lens in conjunction with said objective lens, said second eye-lens forming a second optical axis perpendicular to said first optical axis, wherein an optical distance between said objective lens and said second eye-lens and an optical distance between objective lens and said eye-lens are the same such that a magnification level of said second magnification device is the same as the known level of magnification of the first magnification device; and
an image capture device; and
a light director positioned at an intersection of said first optical axis and said second optical axis, said light director configured to:
transmit a known amount of light entering said objective lens toward said eye-lens; and
reflect a remainder of said light entering said objective lens toward said second eye-lens.

13. The viewing/recording device of claim 12 comprising:
an objective lens filter placed before said objective lens, wherein said light entering said viewing/recording device enters said objective lens filter prior to entering said objective lens; and
an eye-lens filter placed after said eye-lens, wherein said light passes through said eye-lens prior to entering said eye-lens filter; and
a second eye-lens filter after said second eye-lens, wherein said remaining light passes through said second eye-lens prior to entering said second eye-lens filter.

14. The viewing/recording device of claim 12 comprising:
an afocal magnification device in-line with said second magnification device along said second optical axis, said afocal magnification device configured to:
magnify said remaining light after passing through said second magnification device.

15. The viewing/recording device of claim 12 comprising:
a transmitter configured to:
transfer images captured by said image capture device to a receiving system, wherein said transfer is through one of: a wired connection and a wireless connection.

16. The viewing/recording device of claim 12, wherein said light director is one of: a block beam splitter, a plate beam splitter and partially transmissive and partially reflective mirror assembly.

17. The viewing/recording device of claim 12 comprising:
a lighting source configured to emit said light, wherein said lighting source is one of: attached to said eyewear and separate from said eyewear.

18. A magnification device comprising:
a housing comprising:
a first magnification device, said first magnification device comprising
an objective lens; and
an eye-lens, said objective lens and said eye-lens forming a first optical axis, wherein at least a distance between said objective lens and said eye-lens determines a first level of magnification of light entering said housing through said objective lens;
a second magnification device comprising:
a second eye-lens, wherein said second eye-lens forming a second optical axis oriented perpendicular to said first optical axis and at least a distance between said objective lens and said second eye-lens achieves a second level of magnification wherein said second level of magnification is the same as said first level of magnification; and
a light director positioned at an intersection of said first optical axis and said second optical axis between said objective lens and said eye-lens, wherein said light director is configured to:
direct a first portion of light entering said objective lens to said eye-lens; and
direct a second portion of light entering said objective lens to said second eye-lens, wherein said first portion of light is greater than said second portion of light; and
an image capture device configured to:
receive said second portion of light, wherein said second portion of light represents images associated with an object being viewed; and
a transmitter configured to: transfer said images associated with said object being viewed to a receiving device.

19. The magnification device of claim 18, comprising:
an afocal magnification device, said afocal magnification device configured to:
magnify said second portion of light after passing through said second magnification device by a known factor.

20. The magnification device of claim 18, comprising:
an objective filter positioned before the objective lens, wherein said light entering said magnification device passes through said objective filter prior to entering said objective lens;
an eye-lens filter positioned after the eye-lens, wherein said first portion of light passes through said eye-lens prior to entering said eye-lens filter; and
a second eye-lens filter positioned after the second eye-lens, wherein said second portion of light passes through said second eye-lens prior to entering said second eye-lens filter, and wherein said optical density of said objective filter and said eye-lens filter is determined to remove light in an undesired wavelength band below a known threshold value.

* * * * *